United States Patent
Xie et al.

(10) Patent No.: US 8,123,679 B2
(45) Date of Patent: Feb. 28, 2012

(54) ENDOSCOPE APPARATUS

(75) Inventors: Tianyu Xie, Beijing (CN); Atsushi Okawa, Tokyo (JP); Yasushige Ishihara, Tokyo (JP); Toshiaki Watanabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 1172 days.

(21) Appl. No.: 11/897,848

(22) Filed: Aug. 31, 2007

(65) Prior Publication Data
US 2008/0058594 A1 Mar. 6, 2008

(30) Foreign Application Priority Data
Sep. 6, 2006 (JP) ................. 2006-241311

(51) Int. Cl.
*A61B 1/06* (2006.01)

(52) U.S. Cl. ............. 600/160; 600/117; 600/176

(58) Field of Classification Search .......... 600/109, 600/117, 118, 160, 176; 348/65
See application file for complete search history.

(56) References Cited

U.S. PATENT DOCUMENTS

| 2003/0018235 A1* | 1/2003 | Chen et al. ........... 600/109 |
| 2004/0220478 A1* | 11/2004 | Wallace et al. ........ 600/476 |
| 2005/0148854 A1* | 7/2005 | Ito et al. .............. 600/407 |
| 2006/0149134 A1* | 7/2006 | Soper et al. ........... 600/182 |

FOREIGN PATENT DOCUMENTS

| JP | SHO-62-3405 | 1/1987 |
| JP | 03-162818 A | 7/1991 |
| JP | 06-292204 A | 10/1994 |
| JP | 07-113625 A | 5/1995 |

* cited by examiner

*Primary Examiner* — John P Leubecker
*Assistant Examiner* — Christopher Sponheimer
(74) *Attorney, Agent, or Firm* — Scully, Scott, Murphy & Presser, P.C.

(57) ABSTRACT

The invention includes an insertion portion, one end of which is inserted inside a lumen of a subject; an image-acquisition unit for acquiring an image of an interior wall in the lumen as a substantially circular or substantially ring-shaped interior wall image; a transformation processing unit for transforming, in the interior wall image, at least substantially ring-shaped images concerning the interior wall, whose distance from the one end is uniform, to substantially straight-line-shaped or substantially band-shaped images; a distance-measuring unit for measuring a distance moved by the insertion portion relative to the subject; and an image synthesizing unit for joining the transformed images on the basis of the distance moved measured by the distance-measuring unit.

12 Claims, 9 Drawing Sheets

ENDOSCOPE APPARATUS

BACKGROUND OF THE INVENTION

1. Field of the Invention

The present invention relates to an endoscope apparatus.

This application is based on Japanese Patent Application No. 2006-241311, the content of which is incorporated herein by reference.

2. Description of Related Art

In general, known endoscopes include direct-view endoscope which can observe along the direction of the central axis of an insertion portion and side-view endoscopes which can observe around the circumferential direction of the insertion portion.

In side-view endoscopes, various configurations have been proposed for deflecting and emitting light guided along the central axis of the insertion portion to the tip thereof, as well as for deflecting reflected light that is incident from the circumferential direction along the central axis direction (for example, see Japanese Examined Patent Application, Publication No. SHO-62-3405).

BRIEF SUMMARY OF THE INVENTION

In order to realize the object described above, the present invention provides the following solutions.

The present invention provides an endoscope apparatus including an insertion portion, one end of which is inserted inside a lumen of a subject; an image-acquisition unit configured to acquire an image of an interior wall in the lumen as a substantially circular or substantially ring-shaped interior wall image; a transformation processing unit configured to transform, in the interior wall image, at least substantially ring-shaped images concerning the interior wall, whose distance from the one end is uniform, to substantially straight-line-shaped or substantially band-shaped images; a distance-measuring unit configured to measure a distance moved by the insertion portion relative to the subject; and an image synthesizing unit configured to join the transformed images on the basis of the distance moved measured by the distance-measuring unit.

In the aspect of the invention described above, a reflecting portion configured to reflect light incident on the insertion portion from a side face of the insertion portion towards the image-acquisition unit may be provided at the one end of the insertion portion; and the image acquisition unit may acquire an image using the light reflected by the reflecting portion.

In the aspect of the invention described above, a wide-angle optical system may be provided at the one end of the insertion portion; and the image-acquisition unit may acquire an image of the interior wall via the wide-angle optical system.

In the aspect of the invention described above, an image-guiding fiber configured to guide light emitted from the interior wall to another end of the insertion portion may be provided in the insertion portion; and the image-acquisition unit may acquire an image using light emitted from the image-guiding fiber.

In the aspect of the invention described above, the image-acquisition unit may be disposed at the one end of the insertion portion; and a signal line configured to guide image data output from the image-acquisition unit to the transformation processing unit may be provided in the insertion portion.

The aspect of the invention described above may further include an excitation light source configured to emit excitation light for exciting fluorescence from the interior wall; a light-guiding fiber configured to guide the excitation light to the one end of the insertion portion; and a fluorescence filter configured to transmit only the fluorescence excited from the interior wall, wherein the image-acquisition unit acquires an image using the fluorescence transmitted through the fluorescence filter.

In the aspect of the invention described above, the distance measuring unit may include a graduated portion provided with graduations having prescribed intervals, which are provided on the insertion portion, and a measuring unit configured to measure the graduations.

In the aspect of the invention described above, the measuring unit may be an optical sensor.

In the aspect of the invention described above, the measuring unit may be an image sensor.

In the aspect of the invention described above, the distance-measuring unit may be a calculating unit configured to perform an autocorrelation calculation on the basis of the images transformed by the transformation processing unit to calculate the distance moved by the insertion portion relative to the subject.

DETAILED DESCRIPTION OF THE INVENTION

First Embodiment

An endoscope apparatus according to a first embodiment of the present invention is described below with reference to FIGS. 1 to 7.

Figure 1:
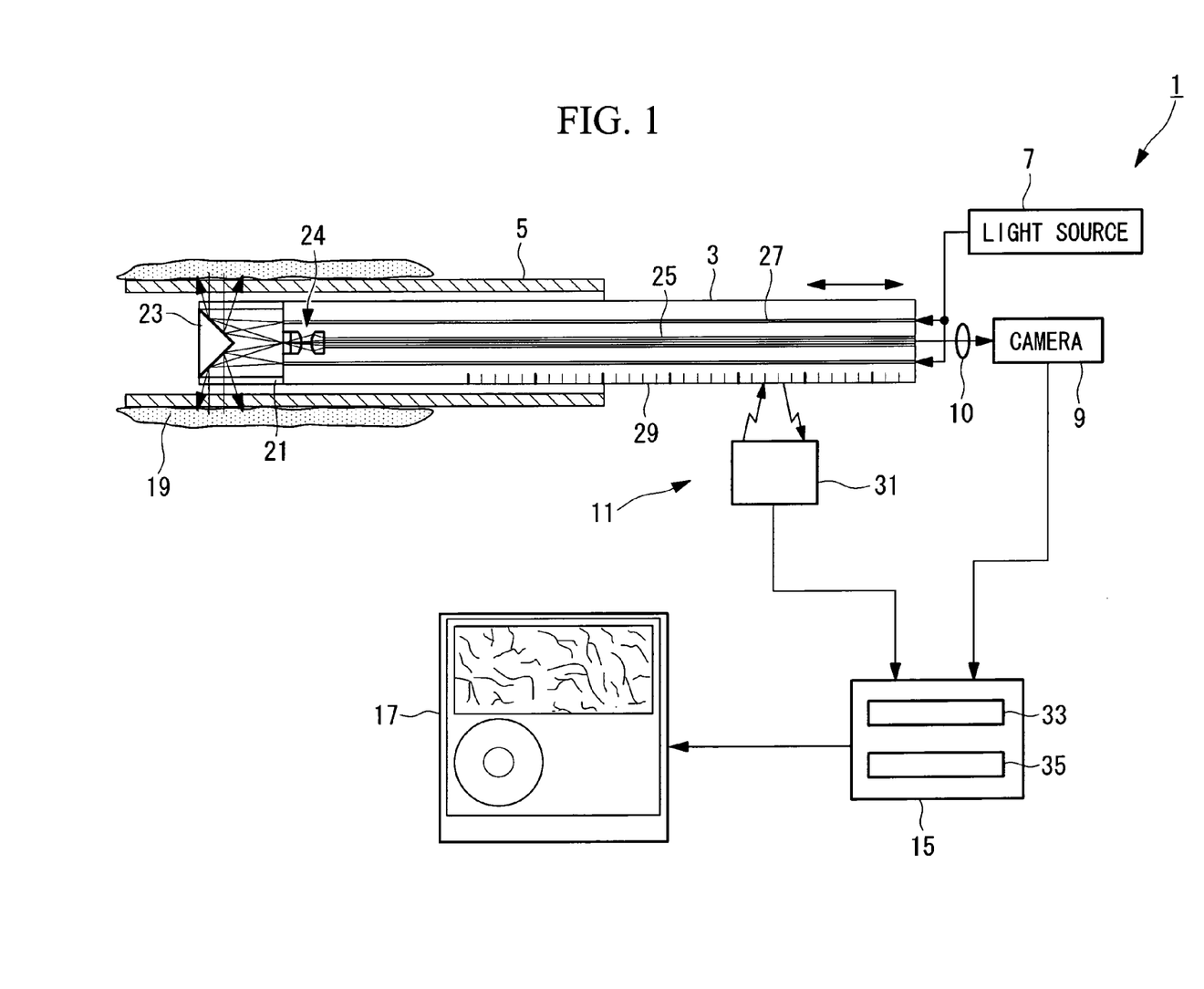
FIG. 1 is a diagram for explaining the overall configuration of an endoscope apparatus according to a first embodiment of the present invention.

FIG. 1 is a diagram for explaining the overall configuration of an endoscope apparatus 1 according to this embodiment.

As shown in FIG. 1, the endoscope apparatus 1 includes an insertion portion 3, a guide tube 5, a light source 7, a camera (image-acquisition unit) 9, a distance-measuring unit 11, an image processing unit (transformation processing unit, image synthesizing unit) 15, and a monitor 17.

The insertion portion 3 is inserted inside a lumen 19 of a subject, which is a substantially cylindrical object, for observing the inner wall of the lumen 19.

The insertion portion 3 is provided with a transparent tube 21, a cone mirror (reflecting portion) 23, an image guiding fiber 25, and a light guiding fiber 27.

An image-acquisition optical system 24 is disposed between the cone mirror 23 and the image-guiding fiber 25. The image-acquisition optical system 24 guides light reflected by the cone mirror 23 to an end face at an insertion end of the image-guiding fiber 25 and forms an image of an internal wall of the lumen 19 at that end face. More specifically, the image-acquisition optical system 24 includes a first lens with positive refractive power and a second lens with positive refractive power, in this order from the cone mirror 23. A first optical member may be substituted for a convex meniscus lens at the cone mirror 23 side, and the first lens and the second lens may be a first lens group and a second lens group each formed of multiple lenses.

The transparent tube 21 is a tube exhibiting optical transparency that is disposed on the insertion portion 3 at an insertion end (one end) to be inserted into the lumen 19.

The cone mirror 23 is a reflecting member disposed at the front end (the left end in FIG. 1) of the transparent tube 21 for reflecting light emitted from the interior wall of the lumen 19 towards the image-guiding fiber 25, which will be described below. The cone mirror 23 is formed to have a substantially conical shape, and the conical surface thereof forms a light reflecting surface. The cone mirror 23 is disposed so that the central axis thereof is substantially coaxial with the image-guiding fiber 25 described below, and the apex thereof opposes the end face of the image-guiding fiber 25.

The image-guiding fiber 25 is an optical fiber bundle or the like for guiding the light reflected by the cone mirror 23 to the camera 9. The image-guiding fiber 25 occupies the central region of the insertion portion 3 and extends along the central axis of the insertion portion 3 from the insertion end to a manipulation end (the other end).

The light-guiding fiber 27 is an optical fiber bundle or the like for guiding illumination light emitted from the light source 7, which is described below, to the insertion end of the insertion portion 3. The light-guiding fiber 27 extends parallel to the central axis of the insertion portion 3 from the insertion end to the manipulation end, in a peripheral region of the insertion portion 3. The illumination light emitted from the insertion end of the light-guiding fiber 27 is reflected at the conical surface of the cone mirror 23 and passes through the transparent tube 21 to illuminate the lumen 19.

The guide tube 5 is a tube exhibiting optical transparency that is disposed between the insertion portion 3 and the lumen 19. The insertion portion 3 is disposed inside the guide tube 5 in such a manner as to be capable of moving in the longitudinal direction. By using the guide tube 5, it is possible to prevent the interior wall of the lumen 19 from moving or deforming as a result of movement of the insertion portion 3.

The light source 7 emits illumination light for illuminating the interior wall of the lumen 19. The light source 7 is disposed at the manipulation end of the insertion portion 3. The illumination light emitted from the light source 7 is incident on the end face at the manipulation end of the light-guiding fiber 27. The light source 7 is not particularly limited, and it is possible to use a known light source.

The camera 9 acquires an image formed by the light emitted from the interior wall of the lumen 19 and outputs image data. The camera 9 is disposed at the manipulation end of the insertion portion 3 and is disposed at a position where the light emitted from the image-guiding fiber 25 is incident. A lens system 10, such as a lens for forming an image on the camera 9, is disposed between the camera 9 and the image-guiding fiber 25. The camera 9 acquires an image of the interior wall of the lumen 19 as a substantially ring-shaped interior-wall image. The camera 9 is not particularly limited; by way of example, an image-acquisition device such as a CCD (Charge Coupled Device) or a CMOS (Complementary Metal Oxide Semiconductor) device may be used. The image data output from the camera 9 is input to the image-processing unit 15.

The distance-measuring unit 11 measures the distance moved by the insertion portion 3 relative to the lumen 19. The distance-measuring unit 11 includes a graduated portion 29 and a sensor unit (measuring unit) 31.

The graduated portion 29 is provided on an outer circumferential surface of the insertion portion 3, in the vicinity of the manipulation end thereof, and graduations are formed thereon at predetermined intervals. The predetermined interval of the graduations is, for example, 200 μm for a normal field of view region in the interior wall of the lumen 19 when using the cone mirror 23; however, it is not particularly limited. Because the graduated portion 29 is disposed in the vicinity of the manipulation end of the insertion portion 3, at least a portion thereof is located outside the lumen 19 even when the insertion portion 3 is inserted deep inside the lumen 19.

The sensor unit 31 detects the distance moved by the insertion portion 3 relative to the lumen 19 by detecting the movement of the graduated portion 29. The sensor unit 31 is disposed at a position opposing the graduated portion 29 and is an optical sensor that detects the intensity of reflected light from the graduated portion 29. More specifically, the sensor unit 31 detects a difference between the intensity of light reflected from the graduations and the intensity of light reflected from regions other than the graduations and outputs detection information concerning the light intensity. The detection information output from the sensor unit 31 is input to the image processing unit 15, which is described later.

The image processing unit 15 synthesizes a developed image on the basis of the image data concerning the interior wall image input from the camera 9 and the detection information input from the sensor unit 31.

The image processing unit 15 is provided with a transformation processing unit 33 and an image synthesizing unit 35.

The transformation processing unit 33 extracts partial image data from the image data concerning the interior wall image and transforms it to image data concerning a band-shaped image. Specifically, the transformation processing unit 33 first extracts part of the image data concerning a substantially ring-shaped interior wall image which is input, for example, image data concerning a uniform-radius ring-shaped image. Then, the transformation processing unit 33 transforms the extracted ring-shaped image data to image data concerning the substantially band-shaped image. Simultaneously with this transformation processing, transformation processing such as image inversion, image stretching at the inner periphery, or image compression at the outer periphery is performed in the transformation processing unit 33.

The image synthesizing unit 35 synthesizes image data concerning the developed image formed by joining image data concerning the substantially band-shaped image transformed by the transformation processing unit 33 on the basis of the detection information from the sensor unit 31. More specifically, the image synthesizing unit 35 joins the image data concerning a plurality of substantially band-shaped images while shifting the placement thereof on the basis of the detection information to synthesize image data concerning a single developed image. The image data concerning the synthesized developed image is output to the monitor 17.

The monitor 17 displays the developed image on the basis of the image data concerning the developed image output from the image synthesizing unit 35.

An observation method used in the endoscope apparatus 1 having the above configuration will be described next.

Figure 2:
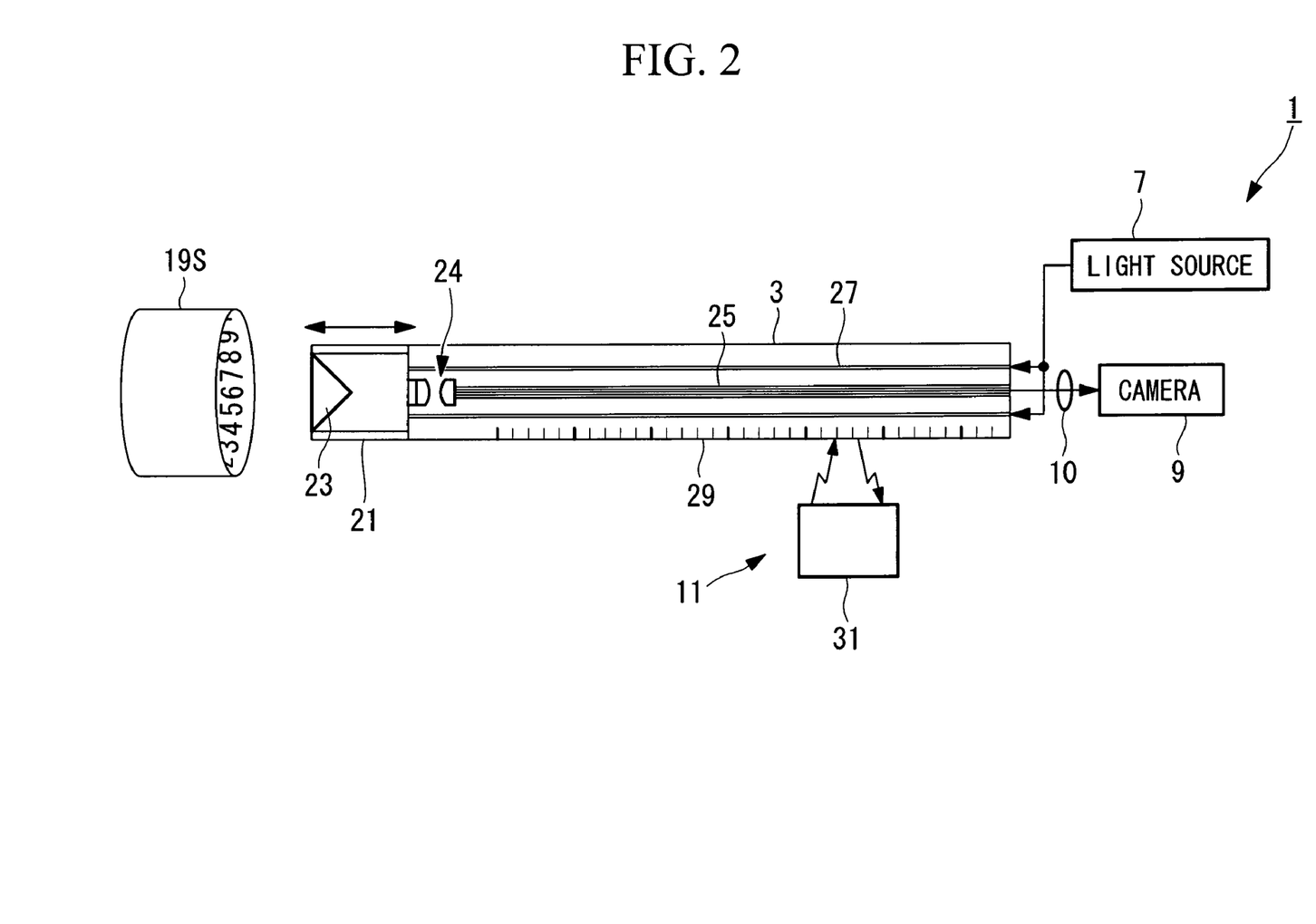
FIG. 2 is a diagram for explaining an observation method used in the endoscope apparatus in FIG. 1.
Figure 3:
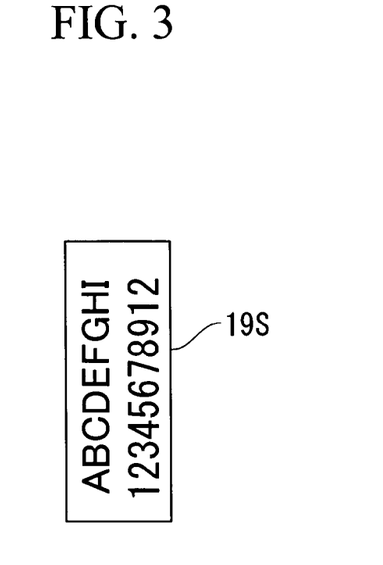
FIG. 3 is a developed view for explaining an interior wall of a lumen sample in FIG. 2.

FIG. 2 is a diagram for explaining the observation method used in the endoscope apparatus in FIG. 1. FIG. 3 is a developed view for explaining the interior wall of a lumen sample in FIG. 2.

Here, for the sake of ease of understanding, a description will be given of an example in which a lumen sample 19S shown in FIG. 2 is observed with the endoscope apparatus 1. As shown in the developed image in FIG. 3, a string of alphabetic characters and a string of Arabic numerals are written on the interior wall of the lumen sample 19S, which is a cylindrical sample.

First, when observing the interior wall of the lumen sample 19S with the endoscope apparatus 1, illumination light is emitted from the light source 7, as shown in FIG. 2. The illumination light enters the light-guiding fiber 27, is guided through the insertion portion 3 to the insertion end thereof, and is emitted towards the cone mirror 23. The illumination light emitted from the light-guiding fiber 27 is reflected by the cone mirror 23 towards the interior wall of the lumen sample 19S. The reflected illumination light passes through the transparent tube 21 and illuminates the interior wall of the lumen sample 19S.

Of the reflected light from the illuminated interior wall of the lumen sample 19S, the reflected light directed towards the central axis of the lumen sample 19S passes through the transparent tube 21 and is incident on the cone mirror 23. The reflected light incident on the cone mirror 23 is reflected towards the end face of the image-guiding fiber 25. The reflected light is guided to the end face at the insertion end of the image-guiding fiber 25 by the image-forming optical system 24, where an image of the lumen sample 19S is formed. The light imaged at the end face at the insertion end of the image-guiding fiber 25 enters the image-guiding fiber 25 through that end face, is guided in the insertion portion 3 to the manipulation end, and is emitted towards the camera 9. The reflected light emitted from the image-guiding fiber 25 is imaged on the image-acquisition device of the camera 9 by the lens system 10.

Figure 4:
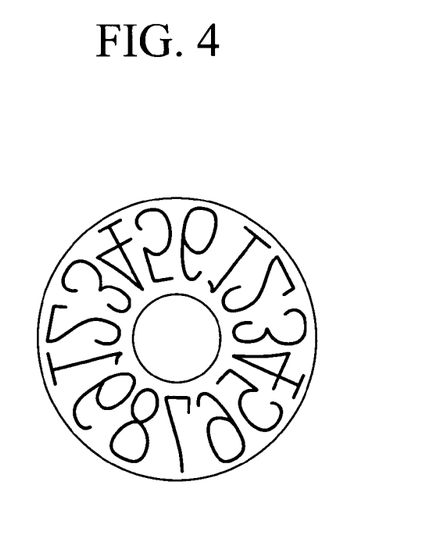
FIG. 4 is a diagram for explaining an image of the lumen sample formed on a camera in FIG. 2.

FIG. 4 is a diagram for explaining the image of the lumen sample formed on the camera in FIG. 2.

The camera 9 acquires an image of the interior wall of the lumen sample 19S formed on the image-acquisition device and outputs image data concerning the interior wall image. The image of the interior wall of the lumen sample 19S is a ring-shaped image, as shown in FIG. 4. FIG. 4 shows an image concerning a string of Arabic numerals; in this image, the Arabic numerals are inverted. The Arabic numerals are arranged around the circumference at the same radius from the center of the image.

The image data concerning the interior wall image output from the camera 9 is input to the image processing unit 15, as shown in FIG. 1. The image data concerning the interior wall image input to the image processing unit 15 is transformed in the transformation processing unit 33. More specifically, a high-image-quality portion of the image data concerning the interior wall, for example, image data concerning the uniform-radius ring-shaped image, is extracted and transformed to image data concerning a substantially strip-shaped image. Simultaneously with this transformation processing, transformation processing such as image inversion, image stretching at the inner periphery, or image compression at the outer periphery is also performed.

Figure 5:
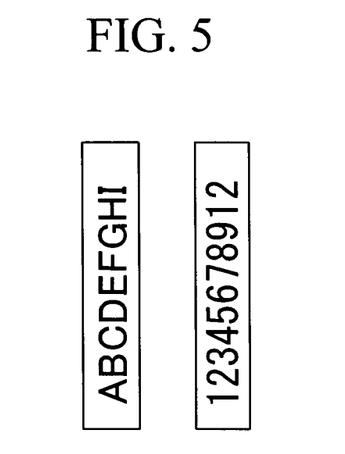
FIG. 5, showing an image of the lumen sample in FIG. 2, is a diagram for explaining an image transformed in a transformation processing unit.

FIG. 5, showing an image of the lumen sample in FIG. 2, is a diagram for explaining an image transformed in the transformation processing unit 33.

An image associated with image data concerning the substantially band-shaped image transformed by the transformation processing unit 33 is developed to a substantially band-shaped image, as shown in FIG. 5. At the same time, the image is inverted relative to the interior wall image, and image distortion is also corrected. In FIG. 5, an image including a string of Arabic numerals is extracted as a first image, and an image including a string of alphabetic characters is extracted as a second image. The width of the extracted images can be set on the basis of the object to be observed. For example, when the size of an affected area etc. of the lumen 19 is about 0.5 mm, it is possible to set the width of the images described above to about 1 mm.

Movement in the longitudinal direction of the insertion portion 3 relative to the lumen sample 19S is detected by the distance-measuring unit 11, as shown in FIG. 2.

More specifically, the movement of the graduated portion 29 provided on the insertion portion 3 is detected by the sensor unit 31. When the graduated portion 29 moves, the graduations of the graduated portion 29 move in front of the sensor unit 31. The intensity of light reflected from the graduated portion 29 and incident on the sensor unit 31 changes due to the movement of the graduations. Because the sensor unit 31 is an optical sensor, it outputs a detection signal based on the intensity of the incident light. The detection signal output from the sensor unit 31 is input to the image synthesizing unit 35 (see FIG. 1). For example, if the intervals of the graduations on the graduated portion 29 are 200 μm, when the sensor unit 31 detects two graduations, it is determined that the insertion portion 3 has moved by 200 μm.

Figure 6:
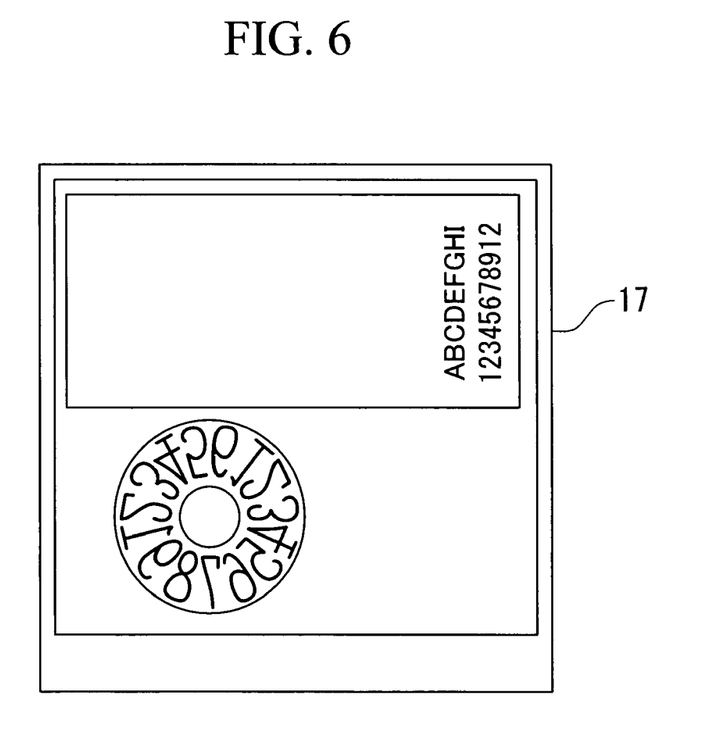
FIG. 6 is a diagram for explaining a display mode of the image of the lumen sample in FIG. 2.

FIG. 6 is a diagram for explaining a display mode of the image of the lumen sample in FIG. 2.

The image data concerning the band-shaped image and the detection signal are input to the image synthesizing unit 35, as shown in FIG. 1. The image synthesizing unit 35 shifts the position of the image data concerning the plurality of substantially band-shaped input images and joins them together to synthesize image data concerning a single developed image. The image data concerning the developed image that is synthesized is output to the monitor 17 and is displayed as shown in FIG. 6. In the case of this embodiment, the developed image of the lumen sample 19S is displayed on the upper half of the monitor 17, and an image based on the image data concerning the interior wall image output from the camera 9 is displayed on the lower half.

According to the configuration described above, because the camera 9, the transformation processing unit 33, and the image synthesizing unit 35 are provided, it is possible to correctly ascertain the presence of an affected area etc. on the interior wall.

The camera 9 can acquire an image of the interior wall in the lumen 19 as a ring-shaped interior wall image. That is, the camera 9 can acquire an image of the entire circumference of the interior wall all at once. In the interior wall image, the transformation processing unit 33 can transform at least a ring-shaped image concerning the interior wall whose distance from the insertion end of the insertion portion 3 is uniform to a substantially band-shaped image. The transformation processing in the transformation processing unit 33 may include image inversion, stretching or compression of a portion of the image, and so forth. The ring-shaped image concerning the interior wall whose distance from the insertion end of the insertion portion 3 is uniform can be, for example, a ring-shaped image with substantially the same radius from the center of the interior wall image. The image synthesizing unit 35 can join the substantially band-shaped images described above. In other words, the image synthesizing unit 35 can synthesize a developed image of the interior wall in the lumen 19.

Therefore, the image obtained from the image synthesizing unit 35 is based on images concerning the interior wall, whose distances from the insertion end of the insertion portion 3 are uniform. As a result, it is possible to evaluate the relative intensity of the light coming from the interior wall, which allows the presence of an affected area or the like to be correctly ascertained.

Since the image obtained from the image synthesizing unit 35 is a developed image of the interior wall in the lumen 19, deformation of the image is small in comparison with a circular or ring-shaped image, and therefore, it is easier to ascertain the presence of an affected area or the like.

Because the distance-measuring unit 11 and the image synthesizing unit 35 are provided, it is possible to accurately identify the position of the affected area found.

The distance-measuring unit 11 measures the distance moved by the insertion portion 3 relative to the subject and outputs the measured distance information to the image synthesizing unit 35. The image synthesizing unit 35 can join the substantially band-shaped images on the basis of the measured distance moved by the insertion portion 3. In other words, the relative positional relationship of the affected area or the like in the interior wall can be made substantially the same as the relative positional relationship of the affected area or the like in the image obtained from the image synthesizing unit 35. As a result, it is possible to accurately identify the position of the affected area found.

By joining the substantially band-shaped images on the basis of the distance moved by the insertion portion 3, the image synthesizing unit 35 can generate a continuous developed image with no discontinuities in the region close to the affected area and can generate discontinuous developed images in other regions.

By providing the cone mirror 23, it is possible to correctly ascertain the presence of an affected area or the like in the interior wall in the lumen 19.

Of the light emitted from the interior wall, the cone mirror 23 can reflect light that is incident on the insertion portion 3 from the side face of the insertion portion 3 towards the camera 9. For the light incident from the side face of the insertion portion 3, the distance between it and the interior wall can easily be kept constant in comparison with light incident from the end face of the insertion end of the insertion portion 3. Therefore, it is possible to evaluate the relative intensity of light emitted from the interior wall, and it is thus possible to correctly ascertain the presence of an affected area or the like.

By using the cone mirror 23, it is possible to make the light emitted from the interior wall towards the center of the lumen 19 incident on the camera 9. Thus, even when the interior wall of the lumen is irregular, it is possible to acquire images right down to the bottom of the irregularities with the camera 9, and it is thus possible to correctly ascertain the presence of an affected area or the like without overlooking it.

Providing the graduated portion 29 and the sensor unit 31 in the distance-measuring unit 11 enables measurement of the distance moved by the insertion portion 3 relative to the subject.

The graduated portion 29 is provided with graduations having a prescribed interval on the insertion portion 3. By measuring the graduations provided on the graduated portion 29, the sensor unit 31 can measure the distance moved by the insertion portion 3 relative to the subject.

Because the sensor unit 31 is an optical sensor, it can measure the distance moved by the insertion portion 3 relative to the subject.

The optical sensor can measure the intensity of the reflected light from the graduated portion 29. The intensity of the reflected light differs depending on whether it comes from portions where the graduations are provided or portions where they are not provided. Thus, by measuring the variations in intensity of the reflected light, the optical sensor can detect the graduations of the graduated portion 29 passing in front of the optical sensor. Therefore, by counting the number of graduations passing in front of the optical sensor, it is possible to measure the distance moved by the insertion portion 3 relative to the subject.

Because the image-guiding fiber 25 is provided and the camera 9 acquires an image using the light emitted from the image-guiding fiber 25, it is possible to reduce the diameter of the insertion portion 3.

The image-guiding fiber 25 guides the light emitted from the interior wall to the manipulation end of the insertion portion 3 and cause that light to be emitted towards the camera 9. The camera 9 can acquire an image using the light emitted from the image-guiding fiber 25. Therefore, compared with an endoscope apparatus in which an image-acquisition unit is provided in the insertion end of the insertion portion 3, in the endoscope apparatus 1 provided with the image-guiding fiber 25 in the insertion portion 3, it is possible to reduce the diameter of the insertion portion 3.

Figure 7:
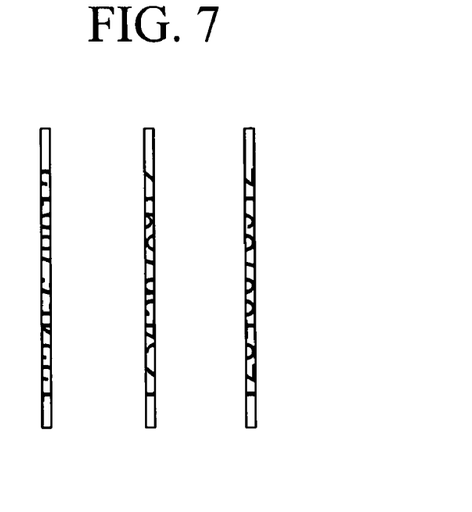
FIG. 7, showing an image of the lumen sample in FIG. 2, is a diagram for explaining another transformation example of an image transformed in the transformation processing unit.

FIG. 7, showing an image of the lumen sample in FIG. 2, is a diagram for explaining another example of transformation of the image in the transformation processing unit.

As described above, in the transformation processing unit 33, the image data concerning the interior wall image may be transformed to image data concerning a substantially band-shaped image. It is not particularly limited, however. As shown in FIG. 7, the image data may be transformed to image data concerning a substantially straight-line-shaped (line-shaped) image.

First Modification of First Embodiment

Next, a first modification of the first embodiment will be described with reference to FIGS. 8 and 9.

The basic configuration of the endoscope apparatus of this modification is the same as that of the first embodiment, but the configuration of the distance-measuring unit is different from that in the first embodiment. In this modification, therefore, only the vicinity of the distance-measuring unit will be described using FIGS. 8 and 9, and a description of other elements will be omitted.

Figure 8:
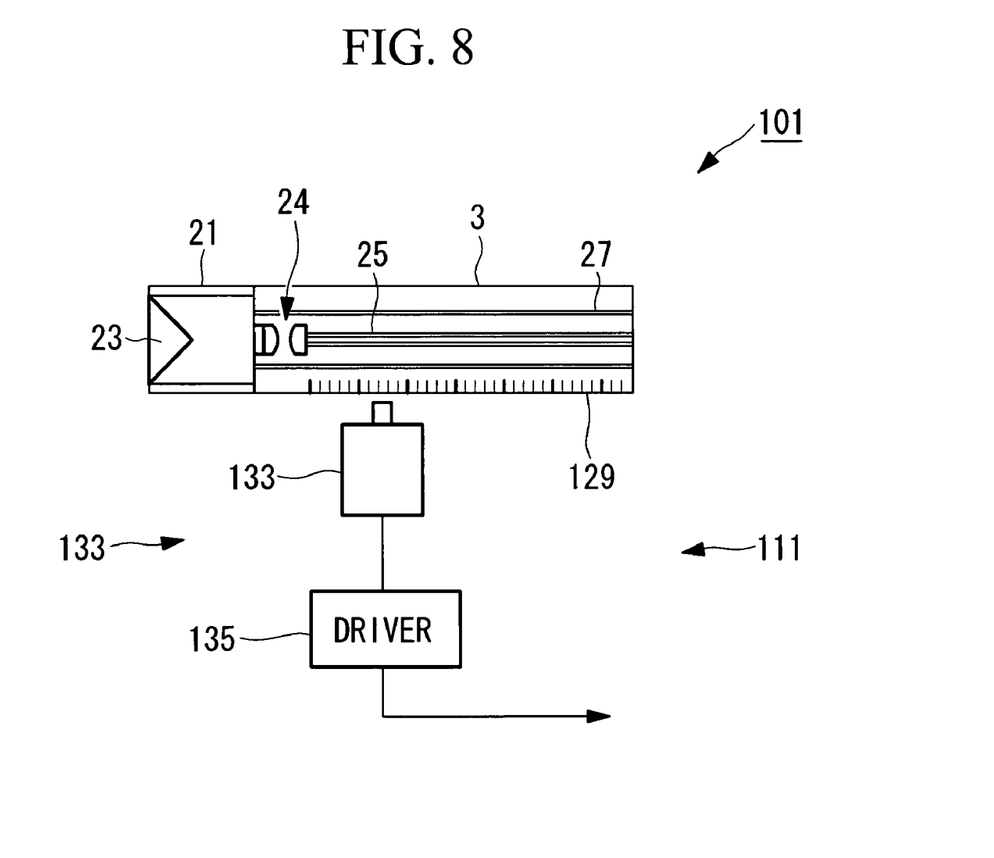
FIG. 8 is a diagram for explaining the configuration of a distance-measuring unit in an endoscope apparatus according to a first modification of the first embodiment of the present invention.

FIG. 8 is a diagram for explaining the configuration of the distance-measuring unit in the endoscope apparatus according to this modification.

Elements that are the same as those in the first embodiment are assigned the same reference numerals, and a description thereof is omitted here.

As shown in FIG. 8, a distance-measuring unit 111 of an endoscope apparatus 101 includes a graduated portion 129 and a sensor unit (measuring unit) 131.

The distance-measuring unit 111 measures the distance moved by the insertion portion 3 relative to the lumen 19.

Figure 9:
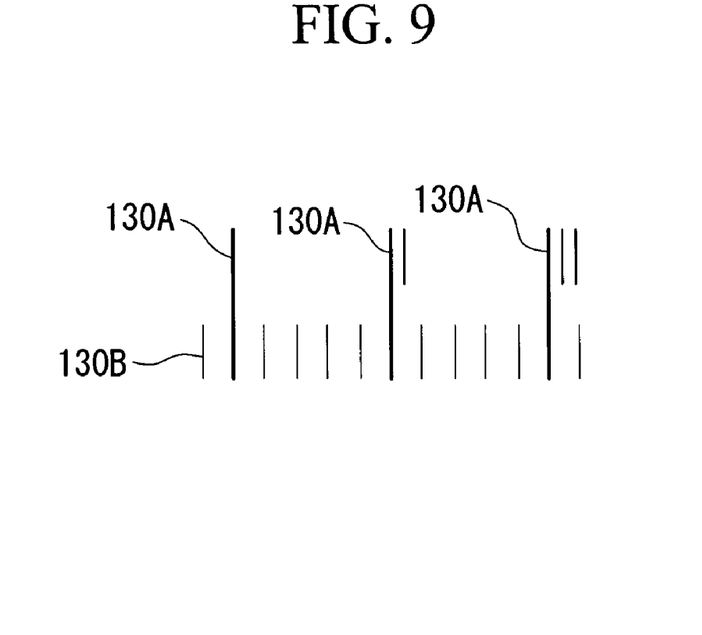
FIG. 9 is a partial magnified view for explaining graduations on a graduated portion in FIG. 8.

FIG. 9 is an enlarged view for explaining graduations on the graduated portion 129 in FIG. 8.

The graduated portion 129, which is provided on the outer circumferential surface of the insertion portion 3, in the vicinity of the manipulation end thereof, has graduations formed thereon at prescribed intervals. The graduations include position-detecting graduations (graduations) 130A and moving-distance-detecting graduations (graduations) 130B. The position-detecting graduations 130A include position information of the insertion portion 3. In this modification, position information of the insertion portion 3 is contained in numbers of lines, which are provided in the position-detecting graduations 130A at the ends where the moving-distance-detecting graduations 130B are not disposed. The moving-distance-detecting graduations 130B are lines disposed at equal intervals between the position-detecting graduations 130A.

By acquiring an image of the graduated portion 129, the sensor unit 131 detects the distance moved by the insertion portion 3 relative to the lumen 19.

As shown in FIG. 8, the sensor unit 131 includes an image sensor 133 and a driver 135. The image sensor 133 is located at a position opposing the graduated portion 129, acquires an image of the position-detecting graduations 130A and the moving-distance-detecting graduations 130B on the graduated portion 129 (see FIG. 9), and extracts an edge pattern thereof. A plurality of the position-detecting graduations 130A and the moving-distance-detecting graduations 130B can be contained within the field of view of the image sensor 133.

The driver 135 drives and controls the image sensor 133 and outputs the edge pattern information output from the image sensor 133 to the image processing unit 15.

Next, an observation method used in the endoscope apparatus 101 configured as described above will be described.

The method of observing the interior wall in the lumen 19 with the camera 9 is the same as that in the first embodiment, and a description thereof is omitted.

The method of measuring the distance moved by the insertion portion 3 with the distance-measuring unit 111 will be described here.

First, the image sensor 133 of the distance-measuring unit 111 acquires an image of the plurality of position-detecting graduations 130A and the moving-distance-detecting graduations 130B on the graduated portion 129 provided on the insertion portion 3. The image sensor 133 extracts an edge pattern of each of the graduations 130A and 130B on the basis of the image of the plurality of position-detecting graduations 130A and the moving-distance-detecting graduations 130B. Information concerning the extracted edge pattern (edge pattern information) is output to the image processing unit 15 via the driver 135.

According to the configuration described above, because the image sensor 133 is provided in the sensor unit 131, it is possible to measure the distance moved by the insertion portion 3 relative to the subject.

The image sensor 133 can detect the shape of the position-detecting graduations 130A and the moving-distance-detecting graduations 130B on the graduated portion 129 which is in front of it. Therefore, by providing position information in part of the shape in the position-detecting graduations 130A, it is possible to detect the relative position of the insertion portion 3 with respect to the subject using the image sensor 133. Thus, by using a method involving calculating the difference from the previously detected relative position, it is possible to measure the distance moved by the insertion portion 3 relative to the subject.

Since the image sensor 133 is used, it is possible to more accurately detect the distance moved by the insertion portion 3 compared to a method using an optical sensor as the sensor unit.

Second Modification of First Embodiment

Next, a second modification of the first embodiment of the present invention will be described with reference to FIGS. 10 and 11.

The basic configuration of the endoscope apparatus of this modification is the same as that of the first embodiment, but the configuration of the distance-measuring unit is different from that in the first embodiment. In this modification, therefore, only the vicinity of the distance-measuring unit will be described using FIGS. 10 and 11, and a description of other elements will be omitted.

Figure 10:
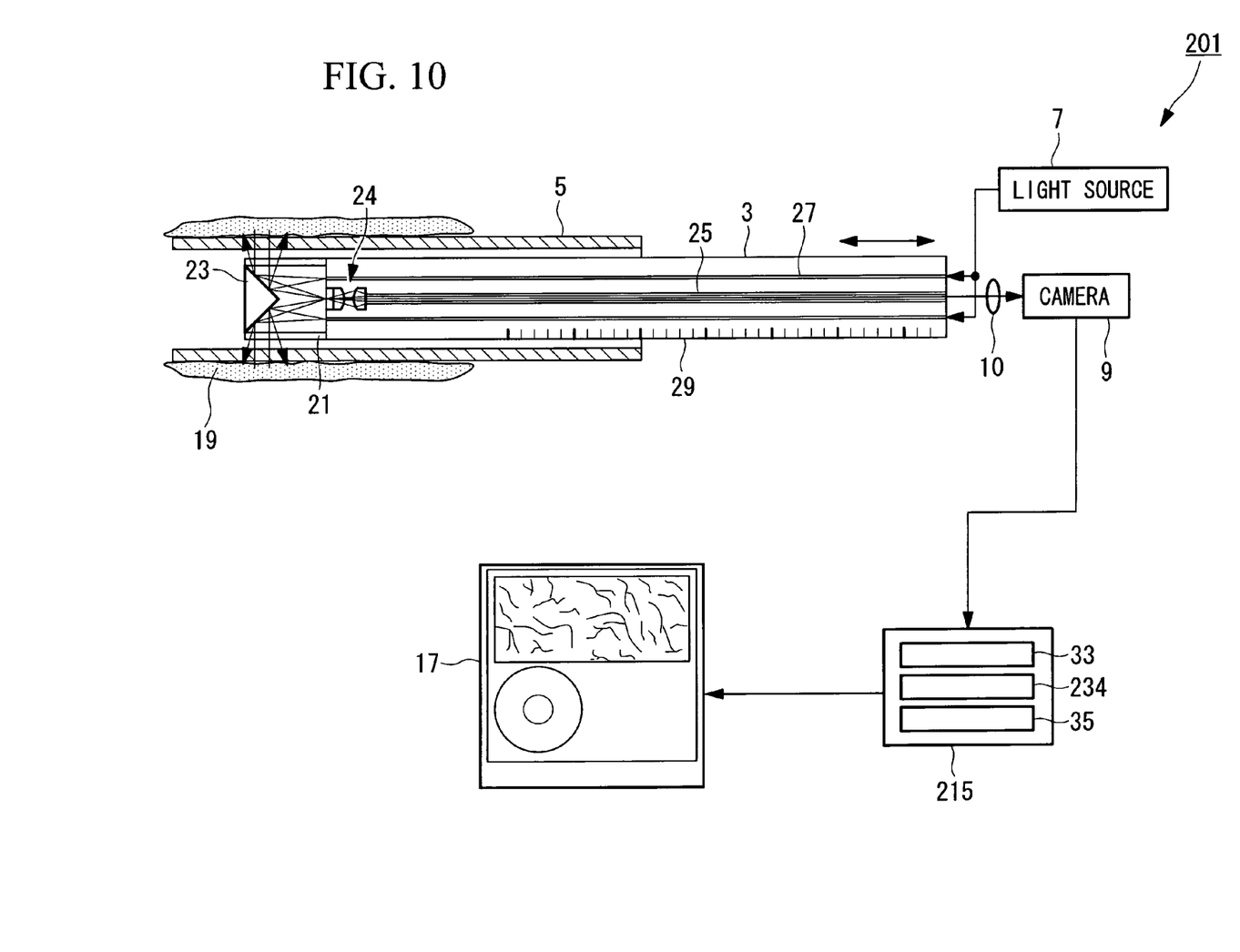
FIG. 10 is a diagram for explaining the configuration of a distance-measuring unit in an endoscope apparatus according to a second modification of the first embodiment of the present invention.

FIG. 10 is a diagram for explaining the configuration of the distance-measuring unit in the endoscope apparatus according to this modification.

Elements that are the same as those in the first embodiment are assigned the same reference numerals, and a description thereof is omitted here.

As shown in FIG. 10, an endoscope apparatus 201 includes the insertion portion 3, the guide tube 5, the light source 7, the camera 9, an image processing unit (transformation processing unit, image synthesizing unit, calculation unit) 215, and the monitor 17.

The image processing unit 215 calculates the distance moved by the insertion portion 3 relative to the lumen 19 on the basis of image data concerning the interior wall, input from the camera 9, and synthesizes a developed image.

The image processing unit 215 is provided with the transformation processing unit 33, a calculation unit (distance-measuring unit) 234, and the image synthesizing unit 35. The calculation unit 234 calculates the distance moved by the insertion portion 3 relative to the lumen 19 on the basis of image data of a plurality of substantially band-shaped images transformed by the transformation processing unit 33.

Figure 11:
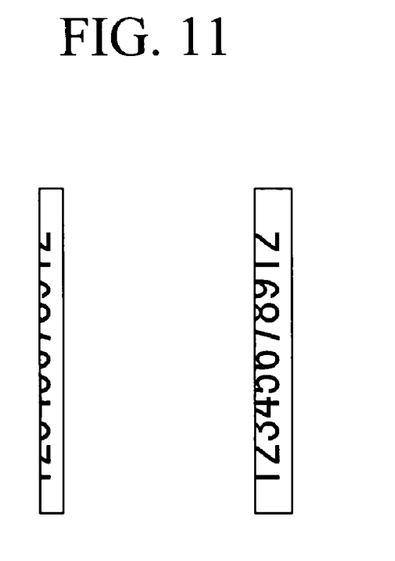
FIG. 11 is a diagram for explaining an image used in calculation in a calculation unit in FIG. 10.

FIG. 11 is a diagram for explaining an image used in the calculation in the calculation unit in FIG. 10.

First, the calculation unit 234 performs autocorrelation processing between two substantially band-shaped images acquired at different times, as shown in FIG. 11, to ascertain whether they contain the same image. Then, the calculation unit 234 measures the amount of motion of the same image contained in the two band-shaped images described above in pixel units of the image. Finally, the calculation unit 234 calculates the distance moved by the insertion portion 3 on the basis of the measured pixel units. Information concerning the calculated distance moved by the insertion portion 3 is input to the image synthesizing unit 34 and is used in synthesizing the developed image.

According to the configuration described above, because the calculation unit 234 is provided in the image processing unit 215, it is possible to determine the distance moved by the insertion portion 3 relative to the subject.

The calculation unit 234 can calculate the distance moved by the insertion portion 3 relative to the subject on the basis of the image data concerning the substantially band-shaped images transformed by the transformation processing unit 33.

It is possible to simplify the construction of the endoscope apparatus 201 compared with a method in which a graduated portion or the like is provided on the insertion portion 3.

Second Embodiment

Next, a second embodiment of the present invention will be described with reference to FIG. 12.

The basic configuration of the endoscope apparatus according to this embodiment is the same as that of the first embodiment, but the configuration of the insertion portion is different from that in the first embodiment. In this embodiment, therefore, only the vicinity of the insertion portion will be described using FIG. 12, and a description of other elements will be omitted.

Figure 12:
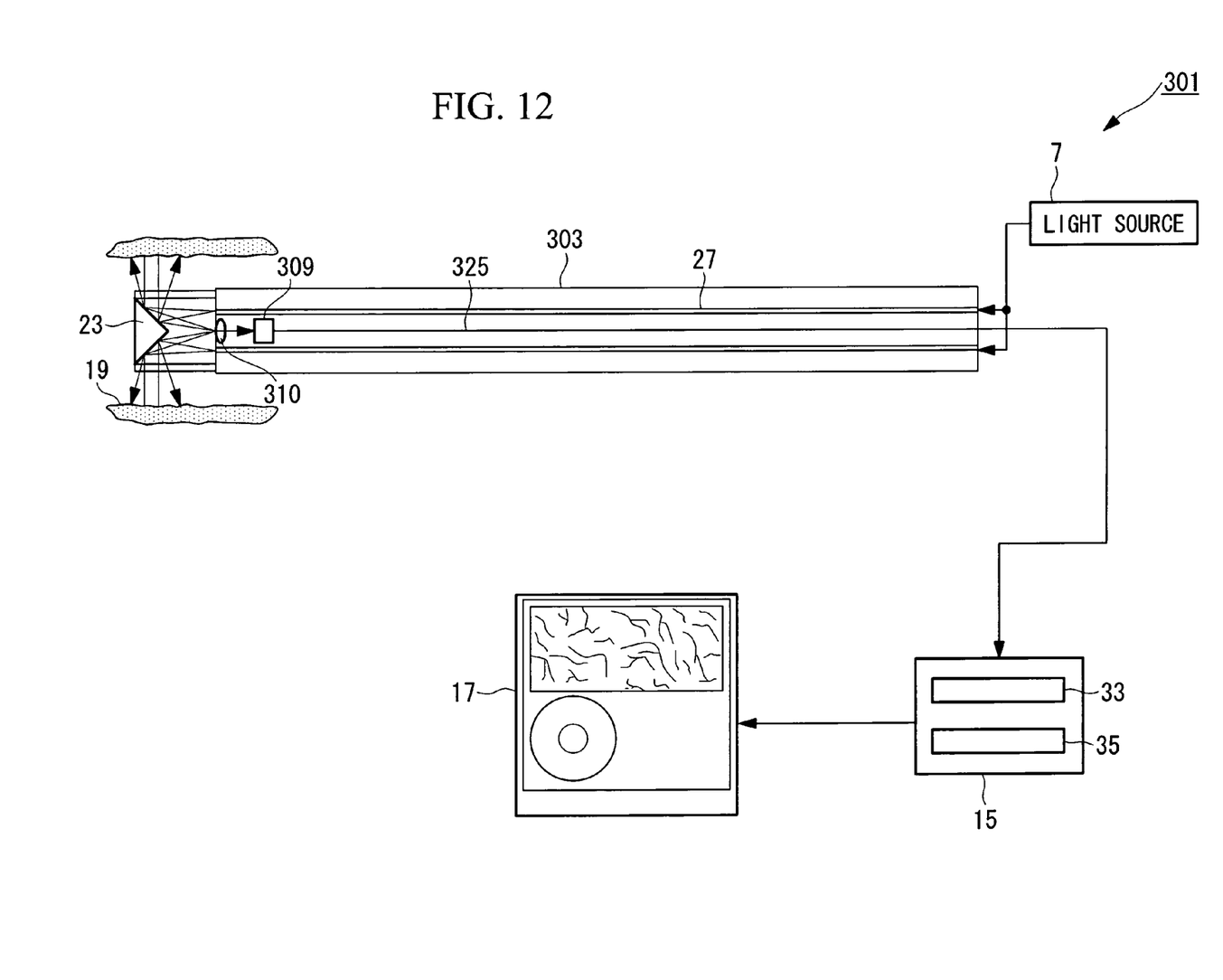
FIG. 12 is a diagram for explaining the configuration of an insertion portion in an endoscope apparatus according to a second embodiment of the present invention.

FIG. 12 is a diagram for explaining the configuration of an insertion portion 303 in the endoscope apparatus according to this embodiment.

Elements that are the same as those in the first embodiment are assigned the same reference numerals, and a description thereof is omitted here.

As shown in FIG. 12, an insertion portion 303 of an endoscope apparatus 301 includes the transparent tube 21, the cone mirror (reflecting portion) 23, a lens system 310, a CCD (image-acquisition unit) 309, a signal line 325, and the light-guiding fiber 27.

The CCD 309 acquires an image using light emitted from the interior wall of the lumen 19 and outputs image data. The CCD 309 is disposed at the insertion end of the insertion portion 3 and is disposed at a position where light reflected at the cone mirror 23 is incident. The lens system 310, for forming an image on the light-receiving surface of the CCD 309, is disposed between the CCD 309 and the cone mirror 23. The CCD 309 acquires an image of the interior wall of the lumen 19 as a substantially ring-shaped interior wall image. The image data output from the CCD 309 is input to the image-processing unit 15 via the signal line 325.

The signal line 325 is for guiding the image data output from the CCD 309 to the image processing unit 15. The signal line 325, which is at the central region of the insertion portion 303, extends along the central axis of the insertion portion 303 from the insertion end to the manipulation end (the other end).

Next, an observation method used in the endoscope apparatus 301 having the above configuration will be described.

The method of illuminating the interior wall of the lumen 19 with the endoscope apparatus 301 is the same as in the first embodiment, and therefore, a description thereof is omitted here.

Of the reflected light from the interior wall of the lumen 19, light directed towards the central axis of the lumen 19 is transmitted through the transparent tube 21 and is incident on the cone mirror 23. The reflected light incident on the cone mirror 23 is reflected towards the CCD 309 and is imaged at the light-receiving surface of the CCD 309 by the lens system 310. The CCD 309 acquires an image of the interior wall of the lumen 19 imaged at the light-receiving surface and outputs image data concerning the interior wall image. The image data concerning the interior wall image, output from the CCD 309, is input to the image processing unit 15 via the signal line 325.

The subsequent operation is the same as in the first embodiment, and therefore, a description thereof is omitted here.

According to the configuration described above, because the CCD 309 is disposed at the insertion end of the insertion portion 303 and because the signal line 325 for guiding the image data output from the CCD 309 to the image processing unit 15 is provided, it is possible to increase the resolution of the image.

The CCD 309 can acquire an image using the light emitted from the interior wall and can output the image data. The CCD 309 can thus directly acquire an image using the light emitted from the interior wall without passing the light through an image guide or the like. The signal line 325 can guide the output image data to the image processing unit 15. Therefore, in comparison with an endoscope apparatus which performs image acquisition via an image guide, the endoscope apparatus 301 which performs direct image acquisition can increase the image resolution.

Third Embodiment

Next, a third embodiment of the present invention will be described with reference to FIG. 13.

The basic configuration of the endoscope apparatus of this embodiment is the same as that of the first embodiment, but the configuration of the insertion portion and the light source is different from that in the first embodiment. In this embodiment, therefore, only the vicinity of the insertion portion and the light source will be described using FIG. 13, and a description of other elements will be omitted.

Figure 13:
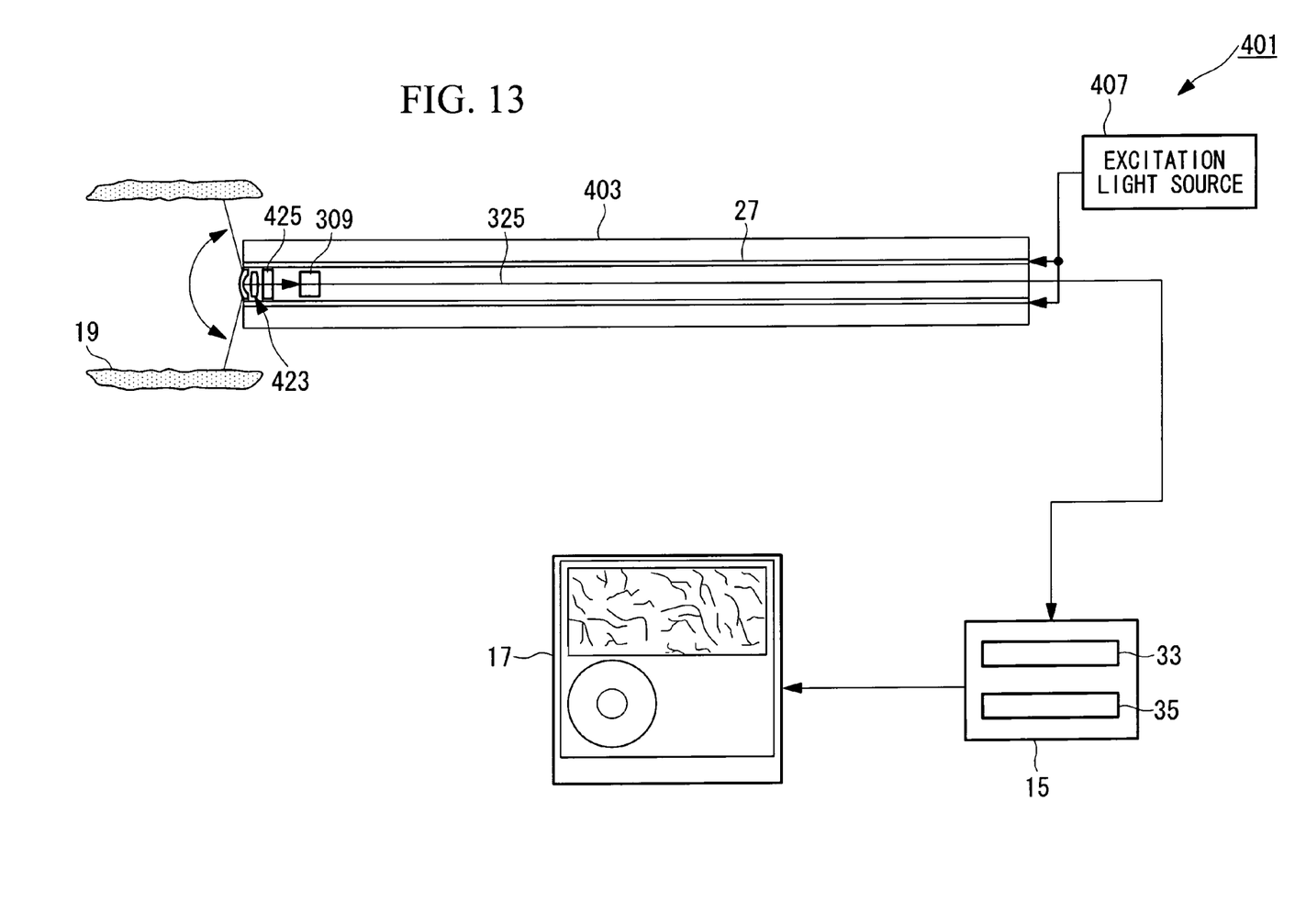
FIG. 13 is a diagram for explaining the configuration of an insertion portion and a light source in an endoscope apparatus according to a third embodiment of the present invention.

FIG. 13 is a diagram for explaining the configuration of the insertion portion and the light source in the endoscope apparatus of this embodiment.

Elements that are the same as those in the first embodiment are assigned the same reference numerals, and a description thereof is omitted here.

An endoscope apparatus 401 in this embodiment ascertains the presence of an affected area in the interior wall of the lumen by administering a drug which accumulates in an affected area in the subject, such as a malignant tumor, and which emits fluorescence in response to excitation light.

As shown in FIG. 13, an insertion portion 403 of the endoscope apparatus 401 is provided with a wide-angle lens system (wide-angle optical system) 423, a fluorescence filter 425, the CCD 3.09, the signal line 325, and the light-guiding fiber 27. An excitation light source 407 that emits excitation light for exciting fluorescence is coupled to the light-guiding fiber 27.

The wide-angle lens system 423 is a lens system for imaging the excitation light reflected from the interior wall of the lumen 19, as well as the excited fluorescence, at the light-receiving surface of the CCD 309. The wide-angle lens system 423, which has a field angle of about 170 degrees, is disposed at the end face of the insertion end of the insertion portion 403.

The fluorescence filter 425 transmits only the fluorescence in the incident excitation light and fluorescence and blocks light in wavelength bands outside that of the fluorescence, such as the excitation light. The fluorescence filter 425 is disposed between the wide-angle lens system 423 and the CCD 309. Therefore, the fluorescence filter 425 allows only the fluorescence to be incident on the CCD 309.

The excitation light source 407 emits excitation light for exciting fluorescence from the drug administered to the subject. The excitation light source 407 is disposed at the manipulation end of the insertion portion 403. The excitation light emitted from the excitation light source 407 is introduced into the light-guiding fiber 27.

Next, an observation method used in the endoscope apparatus 401 having the above configuration will be described.

First, when observing the interior wall of the lumen 19 with the endoscope apparatus 401, excitation light is emitted from the excitation light source 407. The excitation light is introduced into the light-guiding fiber 27, is guided through the insertion portion 403 to the insertion end thereof, and is emitted towards the lumen 19. The emitted excitation light irradiates the interior wall of the lumen 19.

The excitation light is reflected from the interior wall of the lumen 19 irradiated with the excitation light, and the excited fluorescence is emitted from the drug contained in the lumen 19. The excitation light and the fluorescence coming from the lumen 19 enter the wide-angle lens system 423 and are directed towards the light-receiving surface of the CCD 309, to form an image. The excitation light and the fluorescence emitted from the wide-angle lens system 423 are incident on the fluorescence filter 425. The excitation light incident on the fluorescence filter 425 is blocked by the fluorescence filter 425, whereas the fluorescence passes through the fluorescence filter 425 unimpeded. The fluorescence passing through the fluorescence filter 425 forms an image on the light-receiving surface of the CCD 309. The CCD 309 acquires an image concerning the fluorescence emitted from the interior wall described above and outputs image-acquisition data concerning the interior wall image. The output image-acquisition data is input to the image processing unit 15 via the signal line 325.

Since the subsequent operation is the same as that in the first embodiment, a description thereof will be omitted.

According to the configuration described above, because the wide-angle lens system 423 is provided and the CCD 309 acquires an image of the interior wall via the wide-angle lens system 423, it is possible to correctly ascertain the presence of an affected area or the like in the interior wall of the lumen 19.

The wide-angle lens system 423 can cause the light emitted from the interior wall towards the center of the lumen 19 to be incident on the CCD 309. Therefore, even if the interior wall of the lumen 19 is irregular, it is possible to acquire an image right down to the bottom of the irregularities with the CCD 309, which makes it possible to correctly ascertain the presence of an affected area or the like without overlooking it.

Because the light-guiding fiber 27 and the fluorescence filter 425 are provided, it is possible to correctly ascertain the presence of an affected area or the like in the interior wall of the lumen 19 of the subject.

The excitation light source 407 can emit excitation light for exciting fluorescence from the interior wall. The light-guiding fiber 27 can guide the excitation light emitted from the excitation light source 407 to the insertion end of the insertion portion 403 and can emit the excitation light towards the interior wall of the lumen 19. The excitation filter 425 can transmit only the fluorescence excited from the interior wall of the lumen 19 and can block the excitation light and other light. Therefore, the CCD 309 can acquire an image using only the transmitted fluorescence.

Accordingly, in this embodiment in which a drug that accumulates in an affected area and from which fluorescence is excited by the excitation light is administered to the subject, the endoscope apparatus 401 can acquire an image using the fluorescence emitted from the affected area, which makes it possible to correctly ascertain the presence of an affected area or the like.

The present invention is not limited to the embodiments described above. Parts of each of the embodiments described above may be used in combination, and various modifications are also possible.

What is claimed is:

1. An endoscope apparatus comprising:
an insertion portion, one end of which is inserted inside a lumen of a subject;
an image-acquisition unit configured to acquire an image of an interior wall in the lumen as a substantially circular or substantially ring-shaped interior wall image;
a transformation processing unit configured to transform, in the interior wall image, at least substantially ring-shaped images concerning the interior wall, whose distance from the one end is uniform, to substantially straight-line-shaped or substantially band-shaped images;
a distance-measuring unit configured to measure a distance moved by the insertion portion relative to the subject;
an image synthesizing unit configured to join the transformed images on the basis of the distance moved measured by the distance-measuring unit:,
an excitation light source configured to emit excitation light for generating fluorescence from the interior wall;
a light-guiding fiber configured to guide the excitation light to the one end of the insertion portion; and
a fluorescence filter configured to transmit only the fluorescence generated from the interior wall, wherein the image-acquisition unit acquires an image using the fluorescence transmitted through the fluorescence filter.

2. An endoscope apparatus according to claim 1, wherein:
a reflecting portion configured to reflect light incident on the insertion portion from a side face of the insertion portion towards the image-acquisition unit is provided at the one end of the insertion portion; and
the image acquisition unit acquires an image using the light reflected by the reflecting portion.

3. An endoscope apparatus according to claim 1, wherein:
a wide-angle optical system is provided at the one end of the insertion portion; and
the image-acquisition unit acquires an image of the interior wall via the wide-angle optical system.

4. An endoscope apparatus according to claim 1, wherein:
an image-guiding fiber configured to guide light emitted from the interior wall to another end of the insertion portion is provided in the insertion portion; and
the image-acquisition unit acquires an image using light emitted from the image-guiding fiber.

5. An endoscope apparatus according to claim 1, wherein:
the image-acquisition unit is disposed at the one end of the insertion portion; and
a signal line configured to guide image data output from the image-acquisition unit to the transformation processing unit is provided in the insertion portion.

6. An endoscope apparatus according to claim 1, wherein the distance-measuring unit includes a graduated portion provided with graduations having prescribed intervals, which are provided on the insertion portion, and a measuring unit configured to measure the graduations.

7. An endoscope apparatus according to claim 6, wherein the measuring unit is an optical sensor.

8. An endoscope apparatus according to claim 6, wherein the measuring unit is an image sensor.

9. An endoscope apparatus according to claim 1, wherein the distance-measuring unit is a calculating unit configured to perform an autocorrelation calculation on the basis of the images transformed by the transformation processing unit to calculate the distance moved by the insertion portion relative to the subject.

10. An endoscope apparatus comprising:
insertion means, one end of which is inserted inside a lumen of a subject;
image-acquisition means for acquiring an image of an interior wall of the lumen as a substantially circular or substantially ring-shaped interior wall image;

transformation processing means for transforming, in the interior wall image, at least substantially ring-shaped images concerning the interior wall, whose distance from the one end is uniform, to substantially straight-line-shaped or substantially band-shaped images;

distance-measuring means for measuring a distance moved by the insertion portion relative to the subject;

image synthesizing means for joining the transformed images on the basis of the distance moved measured by the distance-measuring means:, an excitation light source configured to emit excitation light for generating fluorescence from the interior wall;

a light-guiding fiber configured to guide the excitation light to the one end of the insertion portion; and a fluorescence filter configured to transmit only the fluorescence generated from the interior wall, wherein the image-acquisition means acquires an image using the fluorescence transmitted through the fluorescence filter.

11. An endoscope apparatus comprising:

an insertion portion, one end of which is inserted inside a lumen of a subject;

an image-acquisition unit configured to acquire an image of an interior wall in the lumen as a substantially circular or substantially ring-shaped interior wall image;

a transformation processing unit configured to transform, in the interior wall image, at least substantially ring-shaped images concerning the interior wall, whose distance from the one end is uniform, to substantially straight-line-shaped or substantially band-shaped images;

a distance-measuring unit configured to measure a distance moved by the insertion portion relative to the subject; and an image synthesizing unit configured to join the transformed images on the basis of the distance moved measured by the distance-measuring unit;

wherein the distance-measuring unit is a calculating unit configured to perform an autocorrelation calculation on the basis of the images transformed by the transformation processing unit to calculate the distance moved by the insertion portion relative to the subject.

12. An endoscope apparatus comprising:

insertion means, one end of which is inserted inside a lumen of a subject;

image-acquisition means for acquiring an image of an interior wall of the lumen as a substantially circular or substantially ring-shaped interior wall image;

transformation processing means for transforming, in the interior wall image, at least substantially ring-shaped images concerning the interior wall, whose distance from the one end is uniform, to substantially straight-line-shaped or substantially band-shaped images;

distance-measuring means for measuring a distance moved by the insertion portion relative to the subject; and image synthesizing means for joining the transformed images on the basis of the distance moved measured by the distance-measuring means;

wherein the distance-measuring means is a calculating means configured to perform an autocorrelation calculation on the basis of the images transformed by the transformation processing means to calculate the distance moved by the insertion means relative to the subject.

* * * * *